US008057843B2

(12) United States Patent
Schlottig et al.

(10) Patent No.: US 8,057,843 B2
(45) Date of Patent: Nov. 15, 2011

(54) IMPLANT, IN PARTICULAR DENTAL IMPLANT

(75) Inventors: Falko Schlottig, Füllinsdorf (CH); Daniel Snétivy, Aesch (CH)

(73) Assignee: Thommen Medical AG, Waldenberg (CH)

( * ) Notice: Subject to any disclaimer, the term of this patent is extended or adjusted under 35 U.S.C. 154(b) by 156 days.

(21) Appl. No.: 12/377,218

(22) PCT Filed: Aug. 17, 2007

(86) PCT No.: PCT/CH2007/000402
§ 371 (c)(1), (2), (4) Date: Feb. 11, 2009

(87) PCT Pub. No.: WO2008/022478
PCT Pub. Date: Feb. 28, 2008

(65) Prior Publication Data
US 2010/0179665 A1    Jul. 15, 2010

(30) Foreign Application Priority Data

Aug. 22, 2006   (CH) ..................................... 1339/06

(51) Int. Cl.
*A61L 33/00* (2006.01)
(52) U.S. Cl. ............ 427/2.24; 427/2; 427/309; 427/327; 427/376.1; 427/419.1; 427/377; 427/255.6; 427/249.15; 148/525; 623/1; 623/1.15; 166/295
(58) Field of Classification Search .............. 427/2, 309, 427/327, 376.1, 419.1, 377, 235, 250, 273, 427/255.6, 249.15, 249.5; 623/1.15, 1, 12; 148/525; 260/37
See application file for complete search history.

(56) References Cited

U.S. PATENT DOCUMENTS

| | | | | | |
|---|---|---|---|---|---|
| 4,882,196 | A | * | 11/1989 | Shimamune et al. | ........ 427/2.27 |
| 5,118,524 | A | * | 6/1992 | Thompson et al. | .......... 427/2.25 |
| 5,306,360 | A | * | 4/1994 | Bharti et al. | .................. 148/525 |
| 6,254,632 | B1 | * | 7/2001 | Wu et al. | ...................... 623/1.15 |
| 2005/0113834 | A1 | * | 5/2005 | Breitenstien et al. | ........... 606/73 |

FOREIGN PATENT DOCUMENTS

| CN | 1 417 378 A | 5/2003 |
|---|---|---|
| JP | 2000-60958 A | 2/2000 |

OTHER PUBLICATIONS

Database WPI Week 200358, Derwent Publications Ltd., London, GB; AN 2003-608626, May 14, 2003, XP002413203.

(Continued)

*Primary Examiner* — Dah-Wei Yuan
*Assistant Examiner* — Andrew Bowman
(74) *Attorney, Agent, or Firm* — Sughrue Mion, PLLC

(57) ABSTRACT

A metal implant, in particular a dental implant, with a hydrophilic surface for at least partial insertion into a bone, and a method for the production of said implant are described. A particularly advantageous hydrophilic surface for improved osteointegration properties is made available if it is briefly treated, at least in some areas, in a weakly alkaline solution. These excellent osteointegration properties can be achieved in a method in which, optionally after a preceding mechanical surface modification by material removal and/or chemical surface modification, at least the areas exposed of this surface exposed to bone and/or soft tissue are chemically modified in an alkaline solution.

18 Claims, 9 Drawing Sheets a)

b)

OTHER PUBLICATIONS

Shigeru Nishiguchi, et al, "Biology of Alkali- and Heat-Treated Titanium Implants", Journal of Biomedical Materials Research—Part A, Oct. 1, 2003, pp. 26-35, vol. 67, No. 1, XP002413201.

Roche Lixikon Medizon, 5. Auflage.

D.M. Brunette, et al., Titanium in Medicine, Springer, pp. 834-836 and 876-888.

Marion L. Maroney, A Guide to Metal and Plastic Finishing, pp. 23-27.

R.K. Pandey, et al., Handbook of Semiconductor Electrodeposition, Marcel Dekker, Inc., pp. 61-122.

George J. Rudzki, Surface Finishing Systems, Metal and Non-Metal Finishing Handbook-Guide, pp. 17-23.

M.J. O'Keefe, et al., Materials and Process for Surface and Interface Engineering/the Science, Technology and Materials Applications of Physical Vapor Deposition Procsses, pp. 151-183.

Dr. Peter Zeggel, Bioactive Calcium Phosphate Coatings for Dental Implants, International Magazine of Oral Implantology Jan. 2000, pp. 52-57.

Jan Eirik Ellingsen, et al., Improved Retention and Bone-To-Implant Contact With Fluoride-Modified Titanium Implants, The International Journal of Oral & Maxillofacial Implants, pp. 659-666.

S.J. Ferguson, et al., Biomechanical Evaluation of the Interfacial Strength of a Chemically Modified Sandblasted and Acid-Etched Titanium Surface, pp. 291-297.

D. Buser, et al., Enhanced Bone Apposition to a Chemically Modified SLA Titanium Surface, pp. 529-533.

F. Rupp, et al., Enhancing Surface Free Energy and Hydrophilicity Through Chemical Modification of Microstructured Titanium Implant Surfaces, pp. 323-334.

* cited by examiner

b)
a)
Fig. 13

IMPLANT, IN PARTICULAR DENTAL IMPLANT

TECHNICAL FIELD

The invention concerns a metallic implant, preferably a dental implant, with a hydrophilic surface for the at least partial insertion into a bone, as well as a method for its production.

BACKGROUND OF THE INVENTION

Injured or damaged parts of the hard and/or soft tissue of the human body are restored the best by using autologous hard and/or soft tissue. This is not always possible for various reasons, which is why in many cases synthetic material is used as a temporary (biodegradable or post-operatively removable, respectively) or permanent replacement material.

Implants which are anchored in hard and/or soft tissue, serve the temporary or permanent replacement or the support of parts of the musculoskeletal system which have been damaged by accident, use, deficiency or disease, or which have been otherwise degenerated, including especially parts of the chewing apparatus. An implant normally is defined as a synthetic chemically stable material, which is introduced into the body as a plastic replacement or for mechanical enforcement (see e.g. Roche Lexikon Medizin, Urban & Fischer (Pubis.); $5^{th}$ edition 2003). The support- and replacement function in the body is taken over on the basis of the mechanical features and the implant design. Hence, for instance hip- and knee joint prostheses, spine implants and dental implants have been clinically used successfully for many years.

For the anchoring of the implant and the compatibility of the implant at the interface between the implant surface/neighboring tissue, the implant surface has a great significance. Hence, measurements have shown that implants with a smooth surface are anchored, almost independently of the basic material used, only a little in the bone (poor osteointegration), while implants with a structured surface enter into a good mechanical and, at a corresponding design of the surface, also a good biological connection with the surrounding hard- or soft tissue (see Titanium in Medicine, Material Science, Surface Science, Engineering, Biological Responses and Medical Applications Series: Engineering Materials, Brunette, D. M.; Tengvall, P.; Textor, M.; Thomsen, P. (Eds.)).

The time necessary for a sufficient incorporation, an important and central feature for implants, is termed osteointegration time, or, in the dental implant field also osseointegration time, respectively. Thereby, the time is described, which passes by until the bone substance has connected with sufficient force and durably with the implant surface, so to speak, until it has virtually integrated into the implant surface.

Various methods are used for surface treatment, see e.g. in A Guide to Metal and Plastic Finishing (Maroney, Marion L.; 1991); Handbook of Semiconductor Electrodeposition (Applied Physics, 5) (Pandey, R. K., et al.; 1996); Surface Finishing Systems: Metal and Non-Metal Finishing Handbook-Guide (Rudzki, George J.; 1984); Titanium in Medicine, Material Science, Surface Science, Engineering, Biological Responses and Medical Applications Series: Engineering Materials, (Brunette, D. M.; Tengvall, P.; Textor, M.; Thomsen, P. (Eds.)); and Materials and Processes for Surface and Interface Engineering (NATO Asi Series. Series E, Applied Sciences, 115, Pauleau, Ives (Editor); 1995); and the references cited therein.

Besides the surface topology the osseointegration of the implant can be influenced by chemical coatings or modifications of the surface. Thereby, implants can be coated in an aqueous solution containing calcium- and phosphate ions. The resulting surface consists of the two calcium phosphate phases hydroxylapatite and bruschite. This coating is post-operatively replaced by young bone directly on the implant surface within 6-10 weeks and results in a very good healing incorporation of the implants (Zeggel P, Bioactive Calcium Phosphate Coatings for Dental Implants, International Magazine Of Oral Implantology, January 2000).

The direct modification of an optimized rough surface with fluoride on titanium implants is described as advantageous for the bone healing process by Ellingsen (Ellingsen, J. E. et al., Improved Retention and Bone to Implant Contact with Fluoride Modified Titanium Implants Int. J. Oral Maxillofac Implants (2004); Vol. 19, p. 659-666).

A chemically active, hydrophilic implant surface on titanium implants can be produced by a very elaborate conservation process in a nitrogen atmosphere. The storage of the surface in a solution of sodium chloride conserves the hydrophilic features. Such a surface shall speed up the process of osseointegration and lead to a higher implant stability in the early phase of osseointegration (Ferguson S. J. et al, Biomechanical evaluation of the interfacial strength of a chemically modified sandblasted and acid-etched titanium surface, Journal of Biomedical Materials Research Part A Volume 78A, Issue 2, pages 291-297). Animal studies of the hydrophilic surface show a significantly higher bone-implant contact compared to a hydrophobic surface at the same surface topography (Buser D. et al, Enhanced Bone Apposition to a Chemically Modified SLA Titanium Surface, J. Dent. Res. 83 (7) 529-533 (2004).). These described hydrophilic features can only be produced in a technologically elaborate way and conserved by a special way of storage, during prolonged contact with air the surface assumes a hydrophobic state. Furthermore, the high costs for production and packaging and the limited storage time in a saline solution are problematic for this technology.

From JP 2000-060958, a method is known, in which an implant is firstly, in a first step, treated with a highly concentrated sodium hydroxide solution with a concentration of 5 mole/l, and then sintered under the influence of heat, and in a second step is treated with a calcium hydroxide solution with a concentration in the range of 0.1-20 mole/l during a time span of 10 min to three days at an increased temperature of more than 50° C., followed by explicit washing. Thereby, presumably apatite is produced on the surface, which is supposed to show advantageous effects for the incorporation of the implant.

SUMMARY OF THE INVENTION

One object of the invention is therefore, to overcome the disadvantages of the state of the art, and to propose implants, which have a hydrophilic surface and which are quickly and lastingly anchored in hard- and soft tissue and thereby show a good osteointegration or osseointegration, respectively. Specifically therefore, an improved implant with a preferably structured and chemically modified surface for the at least partial insertion into hard tissue such as into a bone and/or into soft tissue shall be proposed, wherein the implant is metallic. Furthermore, a suitable production method therefore shall be provided. The solution to this problem is achieved in that the at least section-wise chemically modified and thereby hydrophilic surface is the result of an alkaline surface treatment. Hence, this problem is solved according to the invention, by a specifically treated surface of the implant, said surface thereby having specific features, wherein the treatment can be carried out over the entire surface of the implant as well as on partial sections thereof. Within the scope of this invention, firstly implants are concerned, which are based on metallic materials. It is likewise possible to hydrophilize implants of ceramic basis under the assistance of an alkaline treatment at the surface. This aspect is to be regarded virtually as a separate aspect, which has not been described in the state of the art either, and which has inventive character. Correspondingly, it is also possible to provide a ceramic implant, which has a hydrophilic surface, which is at least section-wise treated in an alkaline manner, or which is the result of a chemical modification, respectively. All embodiments described below correspondingly could likewise be used on ceramic materials, such as for example implants on the basis of zirconium oxide or aluminium oxide or corresponding mixtures.

The terms hydrophilic and hydrophobic describe the wettability of a surface. Thereby, a surface is described as being hydrophilic, if it is wettable, the case of non-wetting is termed to be hydrophobic. The hydrophilic or hydrophobic features can be determined quantatively by contact angle measurements. Therein, the contact angle is defined as the angle which a fluid drop forms on the surface of a solid material to this surface. When using water as a fluid, the surface is termed to be hydrophilic for contact angles under 90°, and hydrophobic for contact angles over 90°. Implants with a rather hydrophilic surface show a better and faster osseointegration (Ferguson S J, Broggini N, Wieland M, de Wild M, Rupp F, Geis-Gerstorfer J, Cochran D L, Buser D.: Biomedical evaluation of the interfacial strength of a chemically modified sandblasted and acid-etched titanium surface; J Biomed mater Res A. 2006 August; 78(2)291-7, as well as Rupp F, Scheideler L, Olshanska N, de Wild M, Wieland M, Geis-Gerstofer J.: Enhancing surface free energy and hydrophilicity through chemical modification of microstructured titanium implant surfaces; J Biomed Mater Res A. 2006 February; 76(2):323-34.

The core of the invention thereby consists in that it has been surprisingly determined that especially metal-based implants, but also ceramic-based implants can be modified by the use of a specific alkaline treatment on the surface, such that they afterwards show excellent osteointegration or osseointegration, respectively. It is shown that the osteointegration or osseointegration, respectively, of a thereby hydrophilized surface is better than the corresponding values for merely blasted and acid-etched surfaces and/or surfaces, especially of metals, which were only provided with a macro- and micro-roughness by sand-blasting and etching.

Hence, the implant is modified at the surface by an alkaline treatment, wherein, especially preferably during the treatment in alkaline solution, essentially exclusively a hydrophilization of the surface is carried out. The treatment in the alkaline solution is carried out especially without connecting an electrical potential, in other words, the implant is very simply immersed in the solution. The surface treatment leads to a hydrophilic surface, which remains hydrophilic for a certain time without additional elaborate storage. In other words, it is not about introducing for example only anions or cations from the alkaline solution into the basic material by the alkaline treatment, or to virtually effect a topographical abrasion, but it is actually about using a chemical process which changes the hydrophilicity of the surface by the alkaline solution, in order to achieve a specifically hydrophilic surface.

Actually, it is also found that the surfaces produced according to the invention, in comparison to treatments according to the state of the art with strongly alkaline solutions (normally in the range of 5M-20M hydroxide-solutions) essentially do not show any topological or topographical structural changes, respectively, which can be attributed to the alkaline treatment.

The hydrophilization of the surface preferably is carried out entirely in an alkaline environment. The alkaline environment can be aqueous or organic alkaline solutions. The surface treatment can possibly be coupled with a mechanically and chemically abrasive treatment for the creation of the topography.

Additional or subsequent coatings, respectively, such as for example of apatite, are not necessary and preferably not present either.

Furthermore, in contrast to the state of the art, post-treatments at a high temperature (e.g. treatment at 600° C. for several hours) or an elaborate rinsing (e.g. in the ultrasound bath) are not necessary. This is especially advantageous with cold-shaped materials, such as e.g. titanium, which otherwise would lose their mechanical properties.

Preferably, an aqueous or organic solution of one or more alkali-hydroxides (especially NaOH) is concerned, wherein preferably a total concentration in the range of 0.05M-0.1M is used.

Alternatively or additionally, strontium can also be used. Hence, an aqueous or organic solution with a strontium-hydroxide can be concerned, wherein preferably a Sr-concentration in the range of 0.05M-0.1M is used.

The hydrophilic surface or the surface modified in an alkaline manner, respectively, is shown to be especially advantageous, if the implant is provided with a coating of metal or metal oxide, respectively, or if, as is preferred, the implant essentially entirely consists of metal. In this context, it must be stressed that the surface of an implant of titanium, zirconium, hafnium, tantalum, niobium, etc., as well as alloys formed thereof (see also below), after contact with oxygen, in other words for example when exposed to air, immediately forms a thin superficial layer of the corresponding oxide. Titanium-implants for example have such a thin layer of titanium (IV)-dioxide ($TiO_2$), with small component parts of $Ti_2O_3$ and TiO. If metallic implants, or their surface, respectively, are mentioned below, this shall accordingly also encompass a surface with such an oxide layer. The metal can be of various types, wherein these are known from the state of the art. For example, a metal can be used, which consists of pure titanium according to ISO 5832. Alternatively, it is possible to use metals, which are known as implant steel according to ISO 5832. It is furthermore possible to use titanium alloys, which comprise, besides titanium, aluminium and/or vanadium and/or niobium. Metals based on cobalt chromium alloys, on cobalt chromium molybdenum alloys, on cobalt chromium tungsten nickel alloys and on cobalt nickel chromium molybdenum titanium alloys, are possible. Furthermore, metals such as tantalum or magnesium or alloys based on tantalum or magnesium, are possible.

According to a preferred embodiment, the implant is a dental implant, the surface of which, in an implanted state being exposed to the bone and/or soft tissue, is at least section-wise hydrophilized. The hydrophilized surface can be created on a topographically pre-structured surface. This can be a sand-blasted surface and/or a surface modified by etching. Furthermore, the present invention concerns a process for the production of an implant, as is described above. The process is characterized in that an implant of metal (or also of ceramics) is surface-modified, possibly after an antecedent abrasive surface modification, especially for the creation of a macro- and micro-roughness (e.g. also in a molten salt), at least in the areas exposed to the bones and/or soft tissue, by the help of an alkaline surface treatment.

Specifically, the process is for the production of a metallic implant with a hydrophilic surface for the at least partial insertion into hard tissue, such as into a bone and/or into soft tissue, characterized in that the process comprises at least one step, in which at least an area designated for the partial insertion into hard tissue, such as into a bone and/or into soft tissue, is subjected to a short-time treatment, possibly after an antecedent mechanically and/or chemically especially abrasive surface modification, in an aqueous or organic solution of alkali- and/or alkaline-earth-hydroxides, or a mixture of these hydroxides, with a total concentration of alkali- and/or alkaline-earth-hydroxide in the range of 0.005M-0.5M. Concentrations in this range are preferred, however, the bottom limit can also lie at 0.008 M, preferably at 0.01 M. Concerning the upper limit, it can also lie at 0.4 M, or at 0.3 M, wherein an upper limit of 0.2 M or 0.1 M is preferred, or especially 0.07 M or 0.05 M. Said bottom limits and upper limits can be combined correspondingly.

A first preferred embodiment is characterized in that, as described above, metal oxides are modified at the surface in the step of alkali- and/or alkaline-earth-hydroxide treatment.

Preferably, an alkaline solution of essentially alkali hydroxides, such as e.g. of potassium hydroxide and/or sodium hydroxide, is used. Small component parts, typically in the range of less than 5% or even less than 2%, of other salts (not only, but preferably of the ones mentioned above) or other additives, can be additionally present for the setting of the hydrophilization conditions.

Preferably, the alkaline solution is an aqueous solution, exclusively consisting of one or more of said hydroxides.

A further preferred embodiment is characterized in that in an aqueous solution of alkali- and/or alkaline-earth-hydroxides, or a mixture of these hydroxides, with a total concentration of alkali- and/or alkaline-earth-hydroxide in the range of 0.05M-0.1M, is subjected to a short-term treatment. Generally, it is preferred that the treatment is carried out during a comparably short time span, e.g. in the range of 1 sec-30 min. It is even possible that the treatment takes place during a time span of in the range of 2 sec-10 min, preferably of 5 sec-120 sec, especially preferably of 5-30 sec.

It is furthermore preferred that the treatment is allowed to take place in an aqueous solution of alkali- and/or alkaline-earth-hydroxides, or a mixture of these hydroxides, at a temperature in the range of −10-110° C., preferably in the range of 10-30°.

A further preferred embodiment is characterized in that the aqueous solution is a solution of sodium hydroxide. Preferably in a concentration of 0.01-0.1 mole, preferably of 0.01-0.07 mole, wherein the treatment preferably is carried out in a range of −10-100° C., especially in the range of 10-30° C. (e.g. RT).

As already mentioned, the process is characterized in that the implant surface can be stored and/or packaged and/or implanted after the treatment with the aqueous solution without any post-treatment at an increased temperature and/or post-treatment by rinsing.

A further embodiment concerns a storage method, which is characterized in that the implant surface is stored and packaged after the treatment with the aqueous solution in an alkaline solution. The alkaline solution can be a solution of preferably exclusively alkali- and/or alkaline-earth-hydroxides, or a mixture of these solutions, especially preferably an aqueous solution of sodium hydroxide, preferably at a concentration of 0.0001-0.9 mole.

A further preferred embodiment is characterized in that before the treatment in the aqueous solution a mechanically abrasive surface modification in the form of a blast-treatment is carried out, especially by sand-blasting, preferably by the use of aluminium oxide-particles with an average particle size of 0.05-0.25 mm or 0.25-0.5 mm, especially preferably with a pressure between 1-10 bar, preferably between 1-6 bar, especially preferably between 2-5 bar. Alternatively or additionally, it is possible, prior to the treatment in the aqueous solution and possibly after such a mechanically abrasive surface modification, to carry out a chemical surface modification, especially by the treatment with preferably concentrated sulphuric acid and/or hydrochloric acid and/or hydrofluoric acid and/or nitric acid or mixtures thereof, preferably at a temperature above room temperature.

The process according to a further embodiment can be characterized in that the aqueous solution is degassed prior to the use as an immersion bath for the implant, especially such that carbonates are removed from the solution. In order to maintain this carbonate-free state, the solution can be stored preferably under an inert gas atmosphere until use.

For the further improvement of the modification of the surface, in addition, ultrasound can generally be connected at least period-wise in the solution during the treatment. It possibly suffices to hold the container with the solution to the wall of an ultrasound bath, preferably the container with the solution for the immersion of the implant is immersed into an ultrasound bath. It is generally shown that it is advantageous to subject the bath to mechanical vibrations during the treatment. An alternative possibility is to use the piezoelectric ultrasound hand-held devices usually available in a dentists' practice (for example for dental cleaning), be it that they are immersed in the bath or are held to the container.

Alternatively or additionally, it is furthermore possible to irradiate the implant with UV-light prior to and/or during and/or after the treatment in the solution.

For certain materials, it is found not to be very easy, also after prolonged storage, to ensure the hydrophilic surface enduringly. Accordingly, the present invention also concerns a method, which is characterized in that an implant, possibly after an antecedent mechanically and/or chemically abrasive surface modification, and which optionally (but in no way mandatorily) has already been treated in an aqueous or organic solution of alkali- and/or alkaline-earth-hydroxides as described above, is sterilely packaged and packaged together with a container containing an aqueous or organic solution of alkali- and/or alkaline-earth-hydroxides, or a mixture of these hydroxides, with a total concentration of alkali- and/or alkaline-earth-hydroxide in the range of 0.005M-0.5M, as described above. Then the implant, after removal from the package, can be treated in the container by a process as described above, just shortly before its insertion into the human body, followed by insertion.

It can generally be of advantage if the storage of the either already treated or not yet treated implant takes place in the dark. Correspondingly, it is preferred, if the container is a container in which the implant is protected from light.

Correspondingly, the present invention also concerns, in the sense of a kit of parts, a combination package containing at least one (sterilely) packaged implant, especially preferably a dental implant, said implant possibly having been subjected to an antecedent mechanically and/or chemically abrasive surface modification, and/or optionally treated in an aqueous or organic solution of alkali- and/or alkaline-earth-hydroxides as described further above, said package further containing at least one container with a sterilely packaged aqueous or organic solution of alkali- and/or alkaline-earth-hydroxides, or a mixture of these hydroxides, with a total concentration of alkali- and/or alkaline-earth-hydroxide in the range of 0.005M-0.5M, in other words essentially with a solution as used in the context of the above described process. Preferably, such a combination package is characterized in that the container contains an aqueous solution of sodium hydroxide at a concentration of 0.008-0.4 mole, preferably of 0.01-0.1 mole, especially preferably of 0.01-0.07 mole, wherein this solution possibly is rinsed with an inert gas prior to the bottling for the removal of $CO_2$ from the solution.

Furthermore, the invention concerns a metallic (or ceramic) implant with a hydrophilic surface for the at least partial insertion into hard tissue, such as into a bone, and/or into soft tissue, characterized in that the hydrophilic metal oxide surface is at least section-wise modified in an alkaline-, preferably weakly alkaline manner.

Furthermore, the invention concerns a metallic (or ceramic) implant with a hydrophilic surface for the at least partial insertion into hard tissue, such as into a bone, and/or into soft tissue, producible or produced by a method as described above. The implant preferably consists, at least at the surface or preferably entirely, of metal oxide and/or metal.

The implant preferably contains titanium and/or titanium oxide, which possibly additionally is alloyed with aluminium and niobium, and/or wherein this alloy contains vanadium instead of niobium.

Preferably, the implant is a dental implant, the surface of which, in the implanted state, being exposed to the bone and/or soft tissue, is hydrophilized in an alkaline manner.

The hydrophilic surface is preferably at least section-wise macro-rough, especially modified by sand-blasting and micro-rough, especially acid-etched.

Furthermore, the invention concerns a use of such an implant, especially produced as described above, as a dental implant, especially as a crown stub, as a threaded piece, a screw and/or a pin.

Further preferred embodiments of the invention are described in the dependent claims.

SHORT DESCRIPTION OF THE FIGURES

The invention shall be further illustrated below by embodiments in connection with the figures, in which:

FIG. 13 shows photographs of the wetting of implants with blood, a) implant not treated according to the invention, b) implant treated according to the invention.

DETAILED DESCRIPTION OF THE PREFERRED EMBODIMENTS

Figure 1:
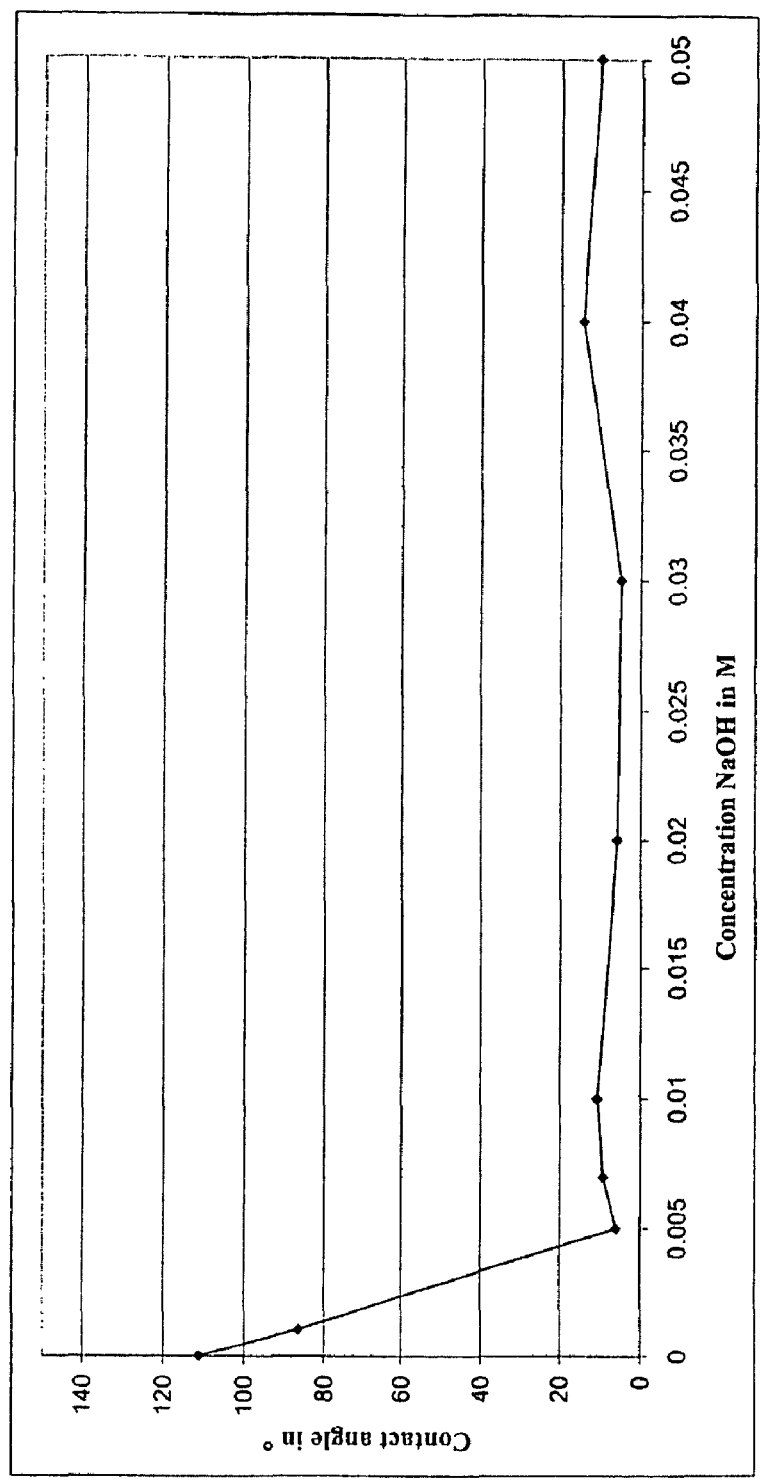
FIG. 1 shows the dependence of the surface hydrophilization (contact angle) on the concentration of the alkaline solution used.

The present invention describes the possibility to chemically modify the surface of implants, which especially are produced from metallic—but also of ceramic materials. Aim of the surface modification are a better anchoring of the implants into hard tissue, a better bond between hard tissue and implant surface, a better bond between soft tissue and implant surface, and a better interaction of the implant surface on the interface between implant surface and hard tissue and/or soft tissue.

Preferably, the invention concerns implants, which are anchored in hard- and/or soft tissue and which serve the temporary or permanent replacement or support of accident-, use-, deficiency- or disease-damaged or otherwise degenerated parts of the musculoskeletal system, including the chewing apparatus, especially the dental area with the corresponding, also aesthetic aspects. Hence, for example hip- and knee joint prostheses, spine implants and dental implants have been used clinically for many years. The problem of the improved osteointegration features, or osseointegration features, respectively, is solved according to the invention by a corresponding surface treatment of the (metal oxide-) surface of the implant, wherein the treatment can be carried out over the entire implant surface as well as over partial areas of the implant surface. By way of such a surface treatment, it is ensured that the metals, such as preferably titanium and its alloys, are better integrated in the hard- and/or soft tissue.

The structural and functional anchoring, e.g. of a dental implant, in the bone, normally is achieved by applying a macro-roughness, and/or a possibly additional micro-roughness. The macro-roughness can for example be obtained by a mechanical blasting process, the subsequent micro-roughness for example in an additive process by plasma technique, or in a subtractive process by chemical etching on the surface. The degree of anchoring of the implant in the bone can be determined with mechanical measurements. Numerous tests have shown that a sufficient anchoring of an implant in the bone depends to a great extent on the surface condition of the implant, especially on the roughness and the chemical environment at its surface.

The present invention describes a specific and newly created (chemical environment for a) hydrophilic surface for the better osteointegration of implants, which are produced of metal, preferably of titanium and its alloys. This biologically effective surface according to the invention can be produced by the use of an alkaline solution, possibly in combination for example with additional mechanical conditioning and structuring, grit blasting, sand blasting and/or subsequent or antecedent chemical treatment, for example etching with acid or similar, or by a combination of such processes.

The surface according to the invention can for example be produced by applying the desired roughness or texture, respectively, to the surface. The implant can especially be produced by grit-blasting or sand-blasting the implant surface, and/or structuring it by the use of plasma technique, and subsequently treating the surface with a chemical process with an alkaline solution until a corresponding hydrophilic surface has been obtained.

As mentioned, the implant is treated with a base or an aqueous or organic alkaline solution, respectively. Bases, according to the definition of Brönsted, are compounds, which take up protons. According to Lewis, bases are molecules or ions with a lone electron pair or an electron-rich multiple bond. The strength of bases can for example be defined over the pKb-value.

However, bases or alkaline solutions have never found application in the present context for the stable hydrophilization of an implant surface in the surprisingly determined concentration range.

It is surprisingly shown that especially with implants on the basis of metal, alkaline solutions result in an excellent hydrophilization of the surface, which is advantageous for the integration in bones or soft tissue, respectively. Preferably, the surface is hydrophilized with a solution of sodium hydroxide in the present application. However, besides the use of a solution of a hydroxide, it is also possible to use solutions on the basis of various hydroxides.

For example aqueous alkaline solutions, preferably of potassium hydroxide or sodium hydroxide, are shown to be especially suitable, wherein the concentration is set in the range of 0.0001 mole to 0.9 mole, preferably in the range of 0.001 to 0.1. It turns out to be especially suitable if the concentration is chosen in the range of 0.01 to 0.07 M. With such weakly alkaline solutions, especially of said components, the treatment is preferably carried out at a temperature in the range of $-10°$-$100°$ C., especially at a temperature in the range of $10°$ C.-$30°$ C.

It can generally be said that typically an alkaline solution with a concentration in the range of 0.001-0.09 M can be used, preferably in the range of 0.01-0.09 M, preferably at a concentration in the range of 0.01-0.07 M.

According to a further preferred embodiment of the method according to the invention, the surface is exposed at least partially over a time span of 2 seconds to 1 hour, preferably from 5 seconds to 10 minutes, especially from 5 seconds to 1 minute, to an alkaline solution, e.g. in the form of a bath. Preferably, a treatment duration of less than one hour, more preferably of at least 5 seconds is used, in order to actually ensure a sufficient hydrophilization of the implant by the alkaline solution.

With implants pre-treated that way, a secure bond to hard- and soft tissue can be created.

EXPERIMENTAL PRODUCTION OF IMPLANTS

Example 1

A common form of a dental implant in the form of a screw of a diameter of 3.5 mm and of a length of 10 mm was produced from titanium cp degree 4. The surface to be inserted into the bone was then provided with a macro-roughness, by sand-blasting it with a particle of $Al_2O_3$ at about 4 bar. Subsequently, the roughened surface was etched at high temperature with a mixture of hydrochloric acid and sulphuric acid, in order to obtain a micro-structuring. After the etching, the implant was treated with pure/deionised water and then washed and rinsed in deionised water. Subsequently, the implant was immersed into an aqueous 0.05 M NaOH-solution for 10 seconds. After the surface was air-dried, one was able to qualitatively determine, by complete wetting with a drop of water, that the surface behaves in a hydrophilic manner.

Example 2

A common form of a dental implant in the form of a screw of a diameter of 3.5 mm and of a length of 10 mm was produced from titanium cp degree 4. The surface to be inserted into the bone was then provided with a macro-roughness, by sand-blasting it with a particle of $Al_2O_3$ at about 4 bar. Subsequently, the roughened surface was etched at high temperature with a mixture of hydrochloric acid and sulphuric acid, in order to obtain a micro-structuring. After the etching, the implant was treated with pure/deionised water and then washed and rinsed in deionised water. Subsequently, the implant was immersed into an aqueous 0.05 M NaOH-solution for 10 seconds. After the surface was air-dried, the implant was stored at room temperature in air for 4 weeks. Subsequently, one was able to qualitatively determine, by complete wetting with a drop of water, that the surface behaves in a hydrophilic manner.

Example 3

A common form of a dental implant in the form of a screw of a diameter of 3.5 mm and of a length of 10 mm was produced from titanium cp degree 4. The surface to be inserted into the bone was then provided with a macro-roughness, by sand-blasting it with a particle of $Al_2O_3$ at about 4 bar. Subsequently, the roughened surface was etched at high temperature with a mixture of hydrochloric acid and sulphuric acid, in order to obtain a micro-structuring. After the etching, the implant was treated with pure/deionised water and then washed and rinsed in deionised water. Subsequently, the implant was immersed into an 0.05 M NaOH for 10 seconds. Subsequently, the implant was stored in an aqueous 0.01M NaOH-solution at room temperature for 4 weeks. The NaOH-solution was rinsed with $N_2$ beforehand, in order to remove $CO_2$ from the solution and to avoid a formation of carbonate during storage. Subsequently, one was able to qualitatively determine, by complete wetting with a drop of water, that the surface behaves in a hydrophilic manner.

Example 4

Titanium in the form of platelets with a diameter of 15 mm was produced from titanium cp degree 4. The surface of the sample bodies was then provided with a macro-roughness, by sand-blasting it with a particle of $Al_2O_3$ at about 4 bar. Subsequently, the roughened surface was etched at high temperature with a mixture of hydrochloric acid and sulphuric acid, in order to obtain a micro-structuring. After the etching, the sample bodies were treated with pure/deionised water and then washed and rinsed in deionised water. Subsequently, the sample bodies were immersed into various aqueous concentrations of NaOH for about 10 seconds. After air-drying the surface for 40 minutes, one was able to quantitatively determine, by contact angle measurements, at which concentration the transition from hydrophobic to hydrophilic behaviour takes place.

FIG. 1 shows the dependency of the surface hydrophilization (contact angle) on the concentration of the alkaline aqueous solution used. It is shown that, starting at completely unexpectedly low concentrations of about 0.005 M, a substantial effect occurs, and that these unexpectedly low concentrations allow a treatment without post-treatment. Post-treatments (rinsing, heat, etc.) are usually necessary at concentrations of 1 M and higher.

Example 5

Titanium in the form of platelets with a diameter of 15 mm was produced from titanium cp degree 4. The surface of the sample bodies was then provided with a macro-roughness, by sand-blasting it with a particle of $Al_2O_3$ at about 4 bar. Subsequently, the roughened surface was etched at high temperature with a mixture of hydrochloric acid and sulphuric acid, in order to obtain a micro-structuring. After the etching, the sample bodies were treated with pure/deionised water and then washed and rinsed in deionised water. Subsequently, the sample bodies were immersed into various aqueous concentrations of NaOH for about 10 seconds. After air-drying the surface, the implant was stored for 4 weeks in air at 30% humidity at room temperature in the dark. Subsequently, one was able to quantitatively determine, by contact angle measurements, at which concentration in water the transition from hydrophobic to hydrophilic behaviour takes place.

Figure 2:
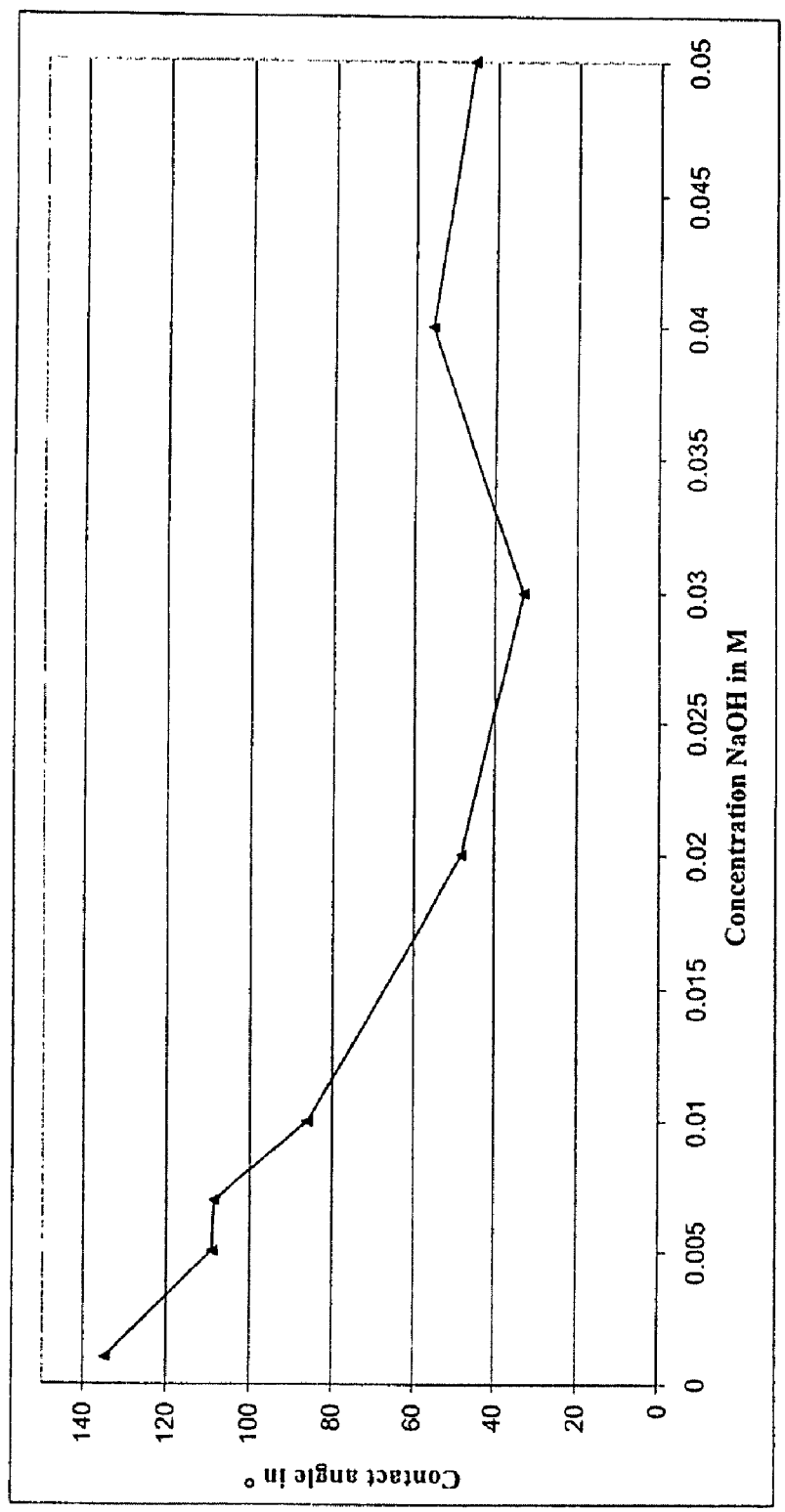
FIG. 2 shows the dependence of the surface hydrophilization (contact angle) on the concentration of the alkaline solution used after storage in air without additional stabilization.

FIG. 2 shows the dependency of the surface hydrophilization (contact angle) on the concentration of the alkaline solution used after such storage in air.

Example 6

Titanium in the form of platelets with a diameter of 15 mm was produced from titanium cp degree 4. The surface of the sample bodies was provided with a macro-roughness, by sand-blasting it with a particle of $Al_2O_3$ at about 4 bar. Subsequently, the roughened surface was etched at high temperature with a mixture of hydrochloric acid and sulphuric acid, in order to obtain a micro-structuring. After the etching, the sample bodies were treated with pure/deionised water and subsequently washed and rinsed in deionised water. Subsequently, the sample bodies were immersed in various aqueous concentrations of NaOH for about 10 seconds. Subsequently, the implant was stored for 4 weeks in 0.01 M NaOH at room temperature. The aqueous NaOH-solution was rinsed with $N_2$ beforehand, in order to remove $CO_2$ from the solution and to avoid a formation of carbonate during the storage. The samples were subsequently removed from the bath and dried for 40 minutes. Subsequently, one was able to quantitatively determine, by contact angle measurements, at which concentration the transition from hydrophobic to hydrophilic behaviour takes place.

Figure 3:
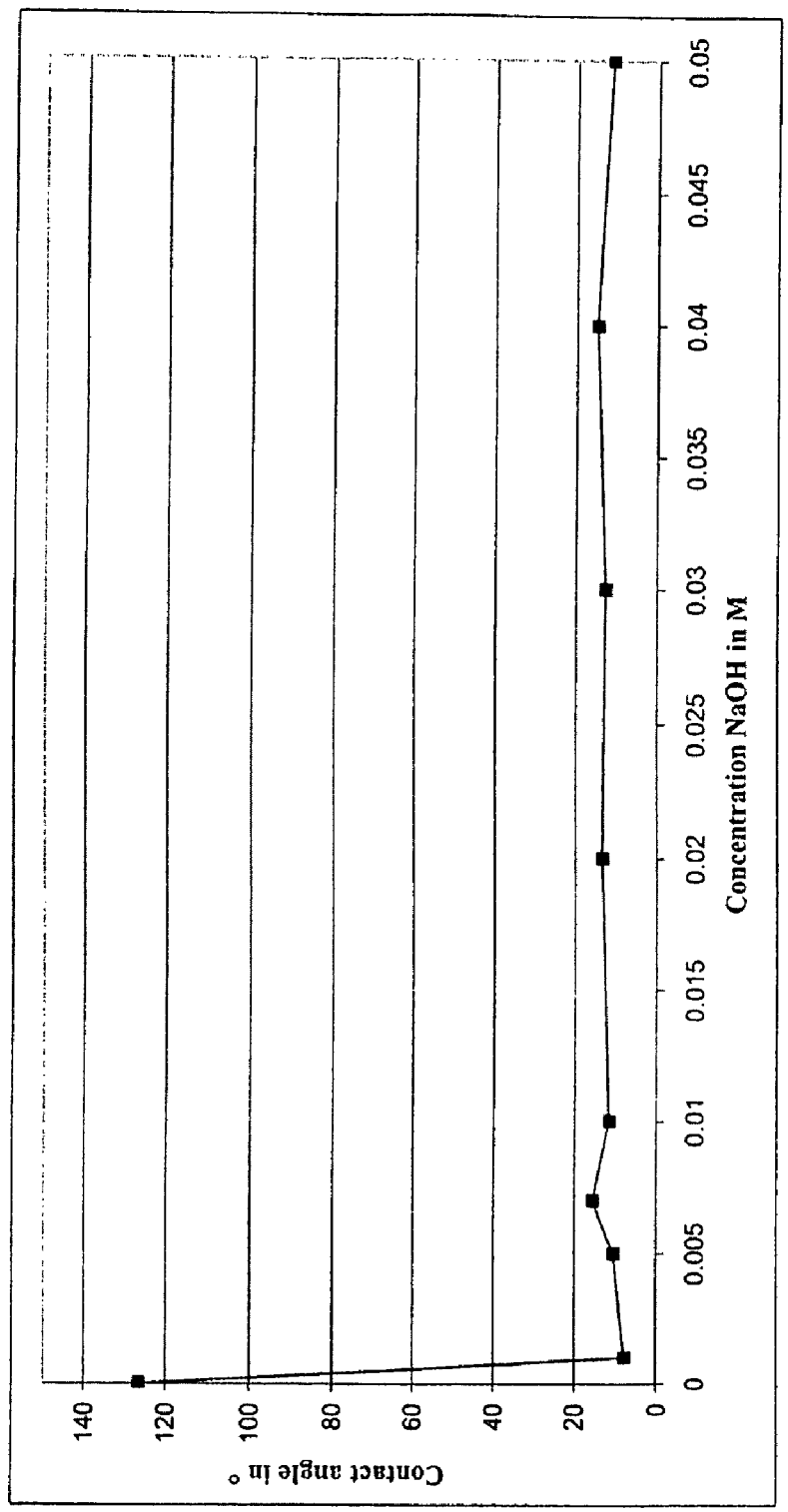
FIG. 3 shows the dependence of the surface hydrophilization (contact angle) on the concentration of the alkaline solution used after storage in alkaline environment.

FIG. 3 shows the dependency of the surface hydrophilization (contact angle) on the concentration of the alkaline solution used after storage in an alkaline environment.

Example 7

A common form of a dental implant in the form of a screw of a diameter of 3.5 mm and of a length of 10 mm was produced from zirconium oxide. The blank shape was made from a cylindrical ceramic blank in an actually known manner of mechanical ceramic treatment, mainly by grinding. The surface to be inserted into the bone was then provided with a macro-roughness, by sand-blasting it with a particle of $Al_2O_3$ of the medium particle size of 0.1-0.15 mm at about 3 bar. Subsequently, the roughened surface (macro-roughness) was treated with a mixture of potassium hydroxide and sodium hydroxide in a molten salt with a ratio of KOH:NaOH of 1:1 at a temperature of over 190° C. for about 30 hours. After the etching, the implant was treated with pure/deionised water in ultrasound and subsequently washed and rinsed in deionised water.

Subsequently, the implant was immersed into an aqueous 0.05 M NaOH-solution for 10 seconds. Subsequently, the implant was stored in 0.01 M NaOH at room temperature for 4 weeks. The NaOH-solution was rinsed with $N_2$ beforehand, in order to remove $CO_2$ from the solution and to avoid a formation of carbonate during the storage. Subsequently, one was able to qualitatively determine, by complete wetting with a drop of water, that the surface behaves in a hydrophilic manner.

Example 8

A common form of a dental implant in the form of a screw of a diameter of 3.5 mm and of a length of 10 mm was produced from zirconium oxide. The blank shape was made from a cylindrical ceramic blank in an actually known manner of mechanical ceramic treatment, mainly by grinding. The surface to be inserted into the bone was then provided with a macro-roughness, by sand-blasting it with a particle of $Al_2O_3$ of the medium particle size of 0.1-0.15 mm at about 3 bar. Subsequently, the roughened surface (macro-roughness) was treated with a mixture of potassium hydroxide and sodium hydroxide in a molten salt with a ratio of KOH:NaOH of 1:1 at a temperature of over 190° C. for about 30 hours. After the etching, the implant was treated with pure/deionised water in ultrasound, and then washed and rinsed in deionised water. After the etching, the implant was treated with pure/deionised water and then washed and rinsed in deionised water.

Subsequently, the implant was immersed into an aqueous 0.05 M NaOH-solution for 10 seconds. After air-drying of the surface, the implant was stored in air at room temperature for 4 weeks. Subsequently, one was able to qualitatively determine, by complete wetting with a drop of water, that the surface behaves in a hydrophilic manner.

Example 9

Titanium dental implants were produced from titanium cp degree 4. The surface of the implants was then provided with a macro-roughness, by sand-blasting it with a particle of $Al_2O_3$ at about 4 bar. Subsequently, the roughened surface was etched at a high temperature with a mixture of hydrochloric acid and sulphuric acid in order to achieve a micro-structuring. After the etching, the implants were treated with pure/deionised water and then washed and rinsed in deionised water. Subsequently, the implants were not treated any further yet and individually packaged. They were subsequently packaged together at a time in a combination package, with a separate, sterilely closed container containing an aqueous NaOH-solution with various concentrations in the range of 0.005-0.5M, preferably 0.005-0.07M. Therein, the size and filling of the container was chosen such that after unpacking the implant was able to be laid into the container, and to subsequently be kept therein for a certain period of time, without any solution escaping over the rim during immersion and wherein the immersed implant ended up lying entirely in the solution with its area to be treated. These combination packages (kit of parts) were subsequently stored for a time span of several weeks.

Shortly before use (for example in the operating room), the implant is unpacked and the container opened (removal of lid), and the implant is subsequently laid into the container, wherein it immerses into the solution entirely for about 10-30 seconds with its area to be treated. After the (optional) air-drying of the surface for several minutes, one was able to qualitatively determine, by complete wetting with a drop of water, that the surface behaves in a hydrophilic manner, and that the still humid or dried implant is ready for its insertion into the human body.

It is by the way also thinkable that the NaOH-solution first is provided in an ampulla in the combination package, and that the solution first is poured into a container provided by the end-user.

Example 10

Titanium dental implants were produced from titanium cp degree 4. The surface of the implants was then provided with a macro-roughness, by sand-blasting it with a particle of $Al_2O_3$ at about 4 bar. Subsequently, the roughened surface was etched with a mixture of hydrochloric acid and sulphuric acid at high temperature in order to achieve a micro-structuring. After the etching, the implants were treated with pure/deionised water and then washed and rinsed in deionised water. Subsequently, the implants were not treated any further yet and individually packaged. They were subsequently packaged together at a time in a combination package, with a separate, sterilely closed container containing an aqueous NaOH-solution with various concentrations in the range of 0.005-0.5M, preferably 0.005-0.07M. Therein, the size and filling of the container was chosen such that after unpacking, the implant was able to be laid or placed into the container or to be held by an instrument, and to subsequently be kept therein for a certain time, without any solution escaping over the rim during immersion and wherein the immersed implant ended up lying partially or entirely in the solution. These combination packages (kit of parts) were subsequently stored during a time span of several weeks. Shortly before use (for example in the operating room), the implant is unpacked and the container opened (removal of lid), and the implant is subsequently laid into the container, wherein it partially or entirely immerses into the solution for about 10-30 seconds. The container containing NaOH is exposed to an ultrasound excitation in an ultrasound bath and (possibly to general mechanical vibrations) during treatment. After the (optional) air-drying of the surface for several minutes, one was able to qualitatively determine, by complete wetting with a drop of water, that the surface behaves in a hydrophilic manner, and that the still humid or dried implant is ready for its insertion into the human body.

The impressive change of the surface was verified in these samples by wetting with blood, and said wetting was photographically captured for implants not dried (see FIG. 13), in comparison to an implant not treated at the surface.

Example 11

Titanium dental implants were produced from titanium cp degree 4 according to example 10 and post-treated. The container containing NaOH however is now not exposed to an ultrasound excitation in an ultrasound bath during treatment, but is exposed to UV-radiation. After the (optional) air-drying of the surface for several minutes, one was able to qualitatively determine, by complete wetting with a drop of water, that the surface behaved in a hydrophilic manner, and that the still humid or dried implant is ready for its insertion into the human body.

Example 12

A common form of a dental implant in the form of a screw of a diameter of 3.5 mm and of a length of 10 mm was produced from titanium cp degree 4 and the surface to be inserted into the bone was treated according to example 10. After the (optional) air-drying of the surface for several minutes, one was able to qualitatively determine, by complete wetting with a drop of water, that the surface behaves in a hydrophilic manner, and that the still humid or dried implant is ready for its insertion into the human body.

Example 13

Disks with a diameter of 15 mm were produced from titanium cp degree 4. The surface comparable to an implant, said surface to be inserted in the bone, was then provided with a macro-roughness, by sand-blasting it with a particle of $Al_2O_3$ at about 4 bar.

Subsequently, the roughened surface was etched with a mixture of hydrochloric acid and sulphuric acid at high temperature in order to achieve a micro-structuring. After the etching, the implant was treated with pure/deionised water and then washed and rinsed in deionised water.

Subsequently, a part of the titanium disks were treated according to JP 2000-060958, discussed above, in the sense of a comparative experiment (V). For this purpose, the samples were immersed in a mixture of 1.5 M NaOH, 1.5 M KOH at a ratio of 1:1 for 24 h at 50° C. in a closed container, and subsequently calcinated at 200° C. for 3 hours. After the probes cooled off, they were immersed according to JP 2000-060958 in 10 mM $Ca(OH)_2$-solution at 80° C. for 1 h, subsequently shortly rinsed in DI-water and dried. The samples thus treated according to JP 2000-060958 were subjected to XPS and ramanspectroscopical tests.

The other part of the titanium disks, prepared as mentioned above, were subjected to the treatment according to the invention (see e.g. example 10). For this purpose, six titanium disks at a time were treated (immersed) with NaOH of concentrations of 0.01; 0.05; 0.005M for 10 seconds each. Furthermore, six titanium disks at a time were treated (immersed) with $Sr(OH)_2$ of the concentrations for 10 seconds each. For this purpose, the container with the NaOH or $Sr(OH)_2$-solution, respectively, was each located in a switched-on ultrasound bath. The samples thus treated according to the invention were also subjected to XPS and ramanspectroscopical tests and compared with the results of the samples treated according to JP 2000-060958.

The tests show the expected clear differences between the hydrophilizing treatment according to the invention and the chemically and structurally surface changing treatment according to JP 2000-060958. The quantification of the XPS-measurements, wherein each sample is measured on two different locations, shows unambiguous differences in the chemical composition of the surface, as can be seen in the following table.

TABLE 1

Quantitative analysis of the XPS-measurements

| Samples JP 2000-060958 | Atomic Concentration [%] | | | | | |
|---|---|---|---|---|---|---|
| | C 1s | Ca 2p | Mg 2p | Na KLL | O 1s | Ti 2p |
| V Sample 1 | 26.3 | 6.5 | 2.9 | 0.4 | 52.3 | 11.7 |
| V Sample 1 | 27.9 | 6.3 | 2.0 | 0.4 | 51.1 | 12.2 |
| V Sample 2 | 27.4 | 6.6 | 2.3 | 0.4 | 52.1 | 11.2 |
| V Sample 2 | 26.6 | 6.2 | 3.7 | 0.3 | 52.4 | 10.8 |

| Samples NaOH | Atomic Concentration [%] | | | | | |
|---|---|---|---|---|---|---|
| | C 1s | N 1s | Na KLL | O 1s | Ti 2p | Zn 2p |
| NaOH 0.01M Sample 1 | 18.6 | 2.7 | 8.5 | 49.1 | 20.7 | 0.4 |
| NaOH 0.01M Sample 1 | 18.3 | 1.8 | 8.7 | 50.4 | 20.3 | 0.5 |
| NaOH 0.01M Sample 2 | 18.5 | 1.9 | 9.0 | 50.5 | 19.8 | 0.4 |
| NaOH 0.01M Sample 2 | 19.3 | 2.5 | 8.4 | 48.6 | 20.8 | 0.3 |
| NaOH 0.05M Sample 1 | 18.8 | 1.9 | 10.2 | 49.7 | 19.0 | 0.3 |
| NaOH 0.05M Sample 1 | 18.6 | 2.1 | 10.9 | 49.9 | 18.1 | 0.4 |
| NaOH 0.05M Sample 2 | 19.2 | 1.8 | 13.7 | 49.2 | 15.9 | 0.2 |
| NaOH 0.05M Sample 2 | 19.6 | 1.8 | 13.4 | 49.1 | 15.9 | 0.2 |
| NaOH 0.005M Sample 1 | 20.3 | 2.0 | 8.6 | 49.9 | 18.6 | 0.6 |
| NaOH 0.005M Sample 1 | 20.4 | 1.6 | 6.7 | 49.9 | 20.9 | 0.5 |
| NaOH 0.005M Sample 2 | 18.3 | 2.4 | 6.0 | 51.4 | 21.7 | 0.4 |
| NaOH 0.005M Sample 2 | 19.3 | 2.4 | 6.0 | 50.0 | 22.1 | 0.2 |

Atomic Concentration [%]

TABLE 1-continued

Quantitative analysis of the XPS-measurements

| Samples Sr(OH)2 | C 1s | Ca 2p | N 1s | O 1s | Sr 3d | Ti 2p | Zn 2p |
|---|---|---|---|---|---|---|---|
| Sr(OH)2 0.01M Sample 1 | 24.2 | 2.0 | 2.8 | 51.0 | 6.0 | 13.6 | 0.5 |
| Sr(OH)2 0.01M Sample 1 | 17.1 | 0.7 | 2.4 | 52.8 | 2.3 | 24.3 | 0.5 |
| Sr(OH)2 0.01M Sample 2 | 19.0 | 0.4 | 3.5 | 50.5 | 2.2 | 24.2 | 0.3 |
| Sr(OH)2 0.01M Sample 2 | 18.5 | 0.3 | 2.3 | 52.4 | 2.5 | 23.8 | 0.3 |
| Sr(OH)2 0.05M Sample 1 | 15.5 | 1.5 | 2.3 | 56.0 | 5.1 | 19.6 | 0.0 |
| Sr(OH)2 0.05M Sample 1 | 18.5 | 1.6 | 1.9 | 53.4 | 7.1 | 17.2 | 0.3 |
| Sr(OH)2 0.05M Sample 2 | 14.6 | 1.3 | 1.5 | 57.9 | 5.2 | 19.2 | 0.3 |
| Sr(OH)2 0.05M Sample 2 | 19.8 | 1.6 | 1.3 | 52.9 | 7.0 | 17.4 | 0.0 |
| Sr(OH)2 0.005M Sample 1 | 17.4 | 0.6 | 2.8 | 52.4 | 1.7 | 24.8 | 0.4 |
| Sr(OH)2 0.005M Sample 1 | 17.3 | 0.4 | 2.3 | 52.5 | 1.8 | 24.8 | 0.8 |
| Sr(OH)2 0.005M Sample 2 | 20.5 | 0.5 | 3.0 | 50.1 | 2.1 | 23.2 | 0.6 |
| Sr(OH)2 0.005M Sample 2 | 19.4 | 0.8 | 2.8 | 50.8 | 2.9 | 22.8 | 0.5 |

The samples treated according to the invention show significantly more titanium on the surface than the samples treated according to JP 2000-060958 and, according to the treatment, a significant portion of Na or Sr, respectively, on the surface, said portion not being present on the surface of titanium disks according to JP 2000-060958.

Contrarily, the samples treated according to JP 2000-060958 have a significantly higher portion of Ca on the surface.

Figure 5:
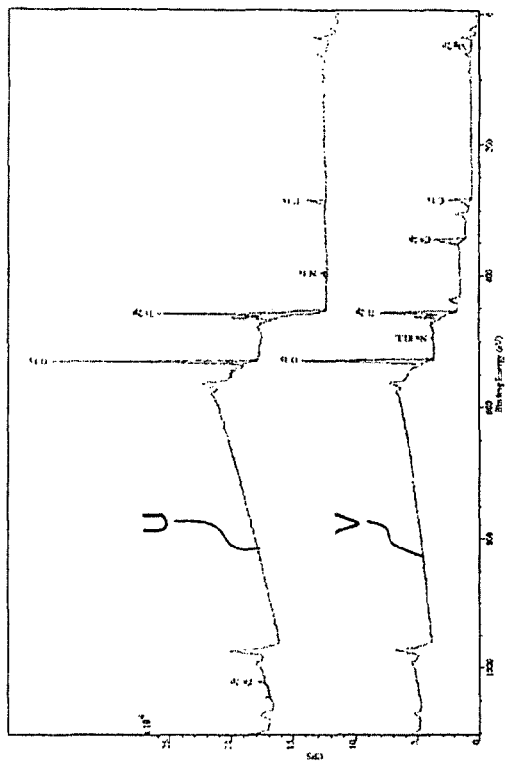
FIG. 5 shows XPS-measurements on an untreated sample (U) and on a comparative sample (V) according to JP 2000-060958.
Figure 6:
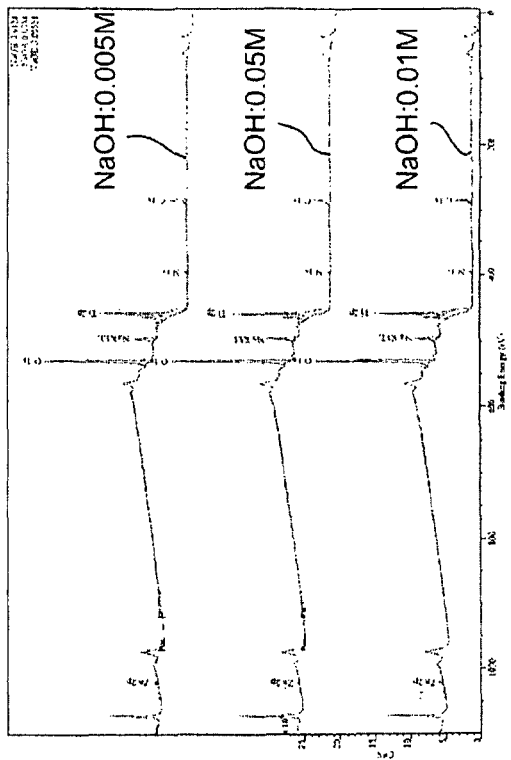
FIG. 6 shows XPS-measurements on NaOH-treated samples according to the invention.
Figure 7:
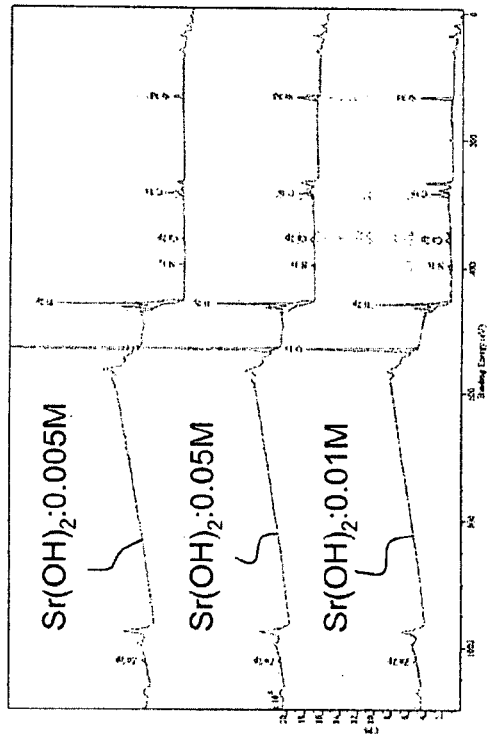
FIG. 7 shows XPS-measurements on $Sr(OH)_2$-treated samples according to the invention.

The XPS-spectra themselves are shown in FIGS. 5 to 8. FIG. 5 shows the spectrum of the samples treated according to JP 2000-060958 as compared to a non-hydrophilized (untreated) sample. FIG. 6 shows the spectra of the samples treated with NaOH according to the invention and FIG. 7 shows the samples treated with Sr(OH)$_2$ according to the invention. The difference concerning Ca, already being clear from the quantification, are clearly shown, and furthermore the different binding energies for titanium.

Figure 8:
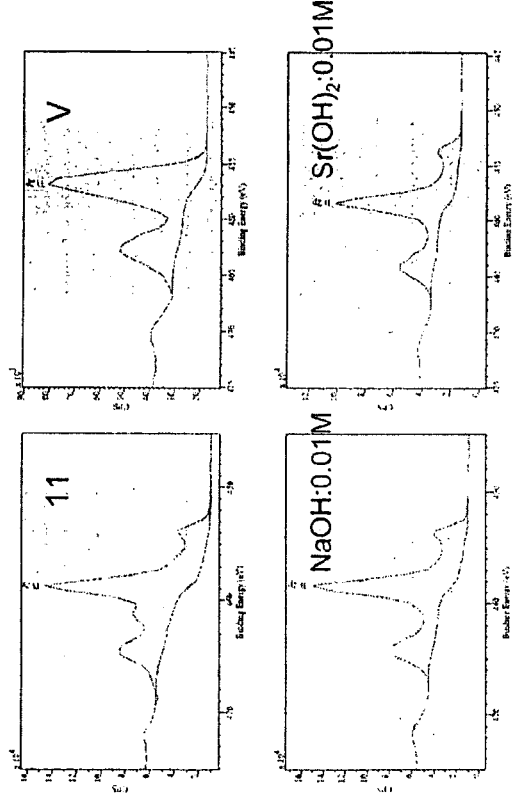
FIG. 8 shows XPS-measurements in detail in the range of titanium on samples a) untreated (U); b) according to JP 2000-060958 (V); c) treated with NaOH according to the invention; d) treated with $Sr(OH)_2$ according to the invention.

Therefore, the detailed spectra were additionally measured for titanium. In FIG. 8, it is clearly visible that the surface treatment according to JP 2000-060958 leads to a change in the chemical environment of titanium.

Contrary thereto, the samples which were surface-treated according to the invention do not show any change in the chemical environment of titanium as to the non-hydrophilized (untreated) surface also shown in the figure.

Experiments by Ramanspectroscopy also show differences between the hydrophilizing treatment according to the invention and the chemically and structurally surface changing treatment according to JP 2000-060958.

Figure 9:
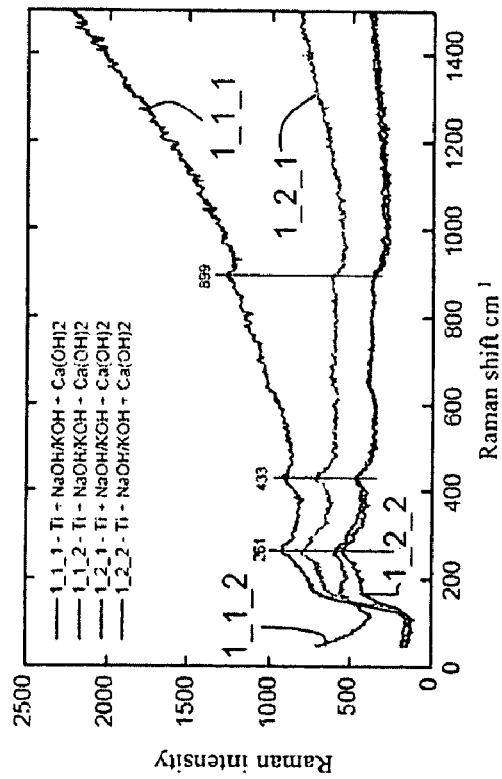
FIG. 9 shows Raman-spectra of the comparative samples according to JP 2000-060958.

In the spectra of the comparative probes 1-1 and 1-2, FIG. 9, (JP 2000-060958 treatment), the broad peaks are observed at 261 cm−1, 433-cm−1, and 663 cm−1, as well as the step at 899 cm−1. These cannot be assigned to the crystalline phases of the titanium oxide (anatase, rutile or brookite) and also not unambiguously to calcium carbonate, calcium titanate or even apatite (contrary to the statement in JP 2000-060958). It probably concerns an amorphic titanium oxide.

Figure 10:
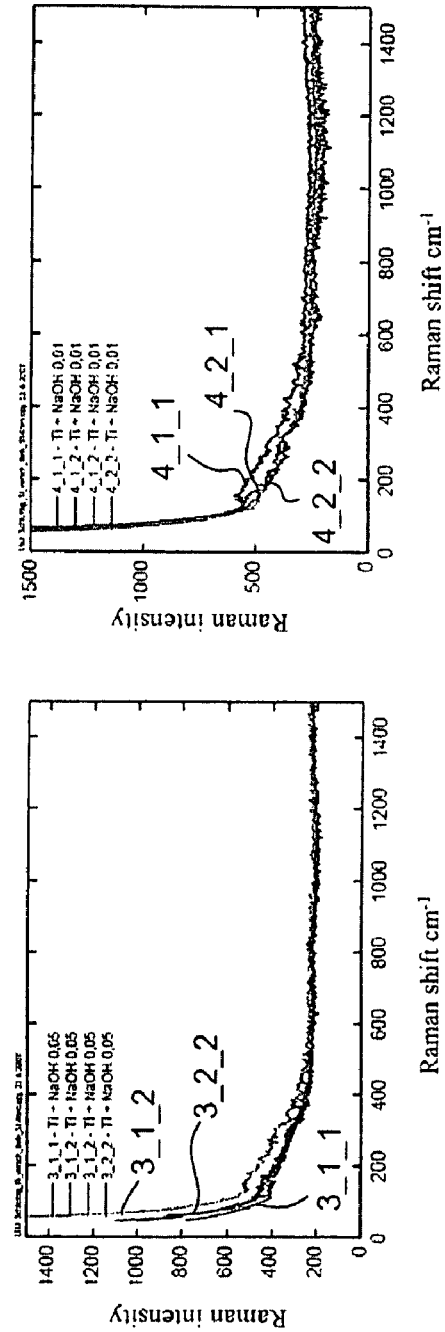
FIG. 10 shows Raman-spectra of NaOH-treated samples according to the invention.
Figure 11:
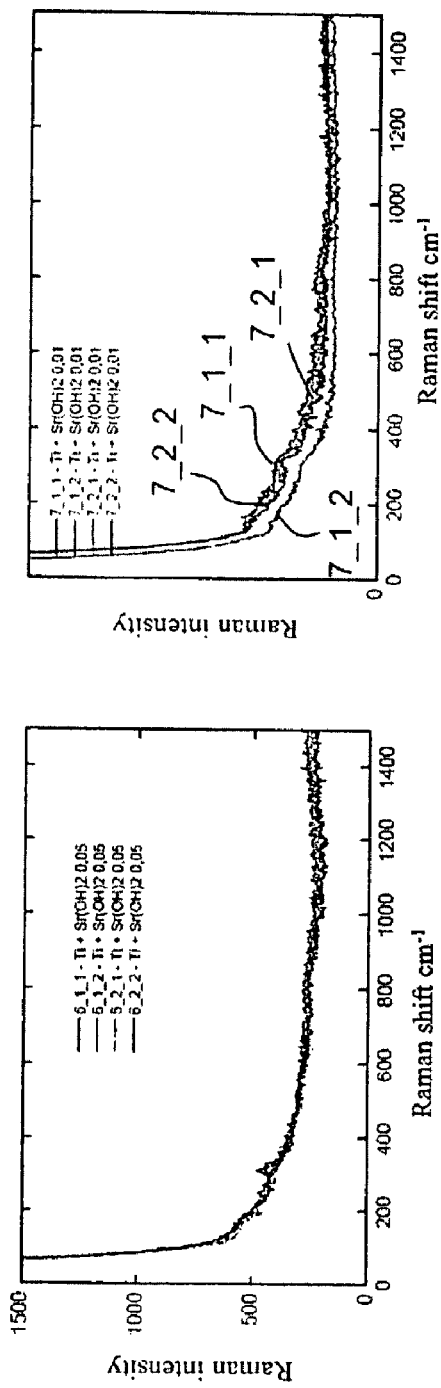
FIG. 11 shows Raman-spectra on $Sr(OH)_2$-treated samples according to the invention.

Contrarily, no Raman peaks at all are detected in the spectra of the hydrophilized samples, as can be seen in FIGS. 10 and 11. Therefore, no Raman-active compounds can be detected on the surface of the samples.

Figure 12:
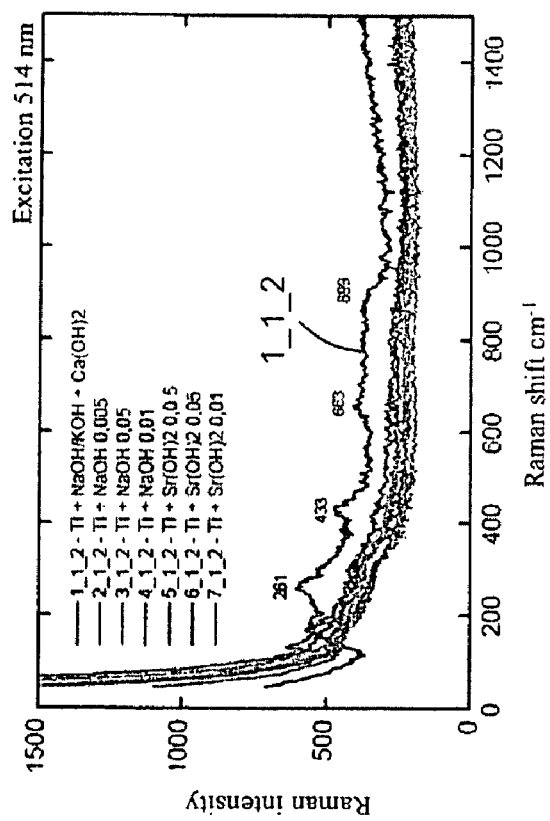
FIG. 12 shows comparative Raman-spectra.

The Raman-spectra of the samples treated according to JP 2000-060958 generally differ from the Raman-spectra of all hydrophilized samples, which are comparable among each other, as can be seen in FIG. 12.

Figure 4:
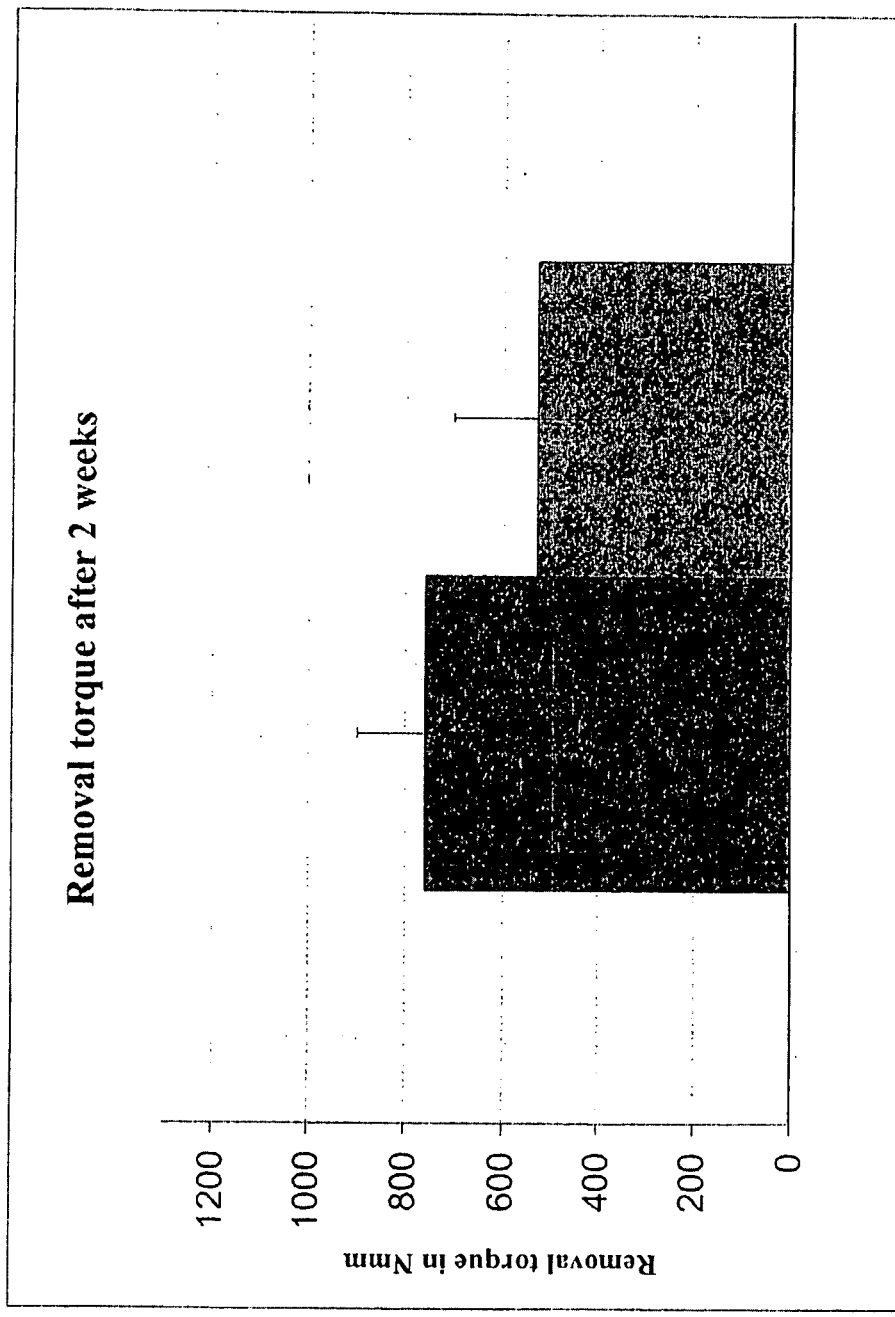
FIG. 4 shows the in vivo results of experiments carried out with two different material- and surface implant types.

In Vivo-Tests:

It has been shown with all exemplarily produced samples with a hydrophilic surface (examples 1 to 13), that the osseointegration or the osteointegration, respectively, was effected well. Furthermore, also a good integration on soft tissue (e.g. gum) is shown. FIG. 4 shows corresponding results of two experiments conducted with two different materials and surface implant types. Therein, a titanium implant with a diameter of 4.2 mm and a length of 8 mm with a surface produced according to the invention essentially according to the above mentioned example 1 (measurement 1 in FIG. 4, on the left) and an accordingly dimensioned dental implant with a plasma-chemically anodically oxidized surface (measurement 2 in FIG. 4, on the right) of a titanium implant were compared. The plasma-chemically anodically oxidized surface corresponds to the surface of commercially very prevalent and often used implants. After a healing time of 2 weeks, the removal torque was determined, which was necessary to loosen the grown-in implants from the bone. As shown in FIG. 4, a better in-growth of the new implant was detected.

Histological measurements furthermore show unambiguously better contact areas (BIC, bone to implant contact) as compared to the implants not treated according to the invention.

The invention claimed is:

1. A method for the production of a metallic implant with a hydrophilic surface for at least partial insertion into hard tissue such as into a bone and/or into soft tissue, wherein the implant, possibly after a prior mechanically and/or chemically abrasive surface modification, is packaged sterilely, and is packaged in a combination package together with a container which contains an aqueous or organic solution of alkali- and/or alkaline-earth-hydroxides, or a mixture of these hydroxides, with a total concentration of alkali- and/or alkaline-earth-hydroxide in the range of 0.005M-0.5M, and wherein the implant is treated in the container by a method comprises at least one step, in which at least one area, which is provided for partial insertion into hard tissue as into a bone and/or into soft tissue, is subjected, optionally after an antecedent mechanically and/or chemically abrasive surface modification, to a short-time treatment in an aqueous or organic solution of alkali- and/or alkaline-earth-hydroxides, or a mixture of these hydroxides, with a total concentration of alkali- and/or alkaline-earth-hydroxide in the range of 0.005M-0.5M after release from the package only shortly before the insertion into the human body.

2. The method according to claim 1, wherein the solution is an aqueous or organic solution of one or more alkali-hydroxides, wherein a total concentration in the range of 0.05M-0.1M is used.

3. The method according to claim 1, wherein the solution is an aqueous or organic solution with a strontium-hydroxide, wherein a concentration in the range of 0.05M-0.1M is used.

4. The method according to claim 1, wherein in the step of the alkali- and/or alkaline-earth-hydroxide treatment, metal oxides are modified at the surface.

5. The method according to claim 1, wherein the alkaline solution is an aqueous solution consisting exclusively of one or more of the named hydroxides.

6. The method according to claim 1, wherein the short-term treatment is carried out in an aqueous solution of alkali- and/or alkaline-earth-hydroxides, or a mixture of these hydroxides, with a total concentration of alkali- and/or earth-alkali hydroxide in the range of 0.05M-0.1M.

7. The method according to claim 1, wherein the treatment is carried out in an aqueous solution of alkali- and/or earth-alkali hydroxides, or a mixture of these hydroxides, during a time span in the range of 1 sec-30 min.

8. The method according to claim 1, wherein the treatment is carried out during a time span in the range of 5 sec-120 sec.

9. The method according to claim 1, wherein the treatment is carried out in an aqueous solution of alkali- and/or alkaline-earth-hydroxides, or a mixture of these hydroxides, at a temperature in the range of 10-30°.

10. The method according to claim 1, wherein the aqueous solution is a solution of sodium hydroxide.

11. The method according to claim 8, wherein the solution is a solution of sodium hydroxide at a concentration of 0.01-0.07 mole, wherein the treatment is carried out at a temperature in the range 10-30° C. or at room temperature.

12. The method according to claim 1, wherein the implant surface is stored or packaged after the treatment with the aqueous solution without any post-treatment with an increased temperature or any post-treatment by rinsing.

13. The method according to claim 1, wherein the aqueous solution is degassed prior to its use as an immersion bath for the implant, and optionally is stored in an inert gas atmosphere until use.

14. The method according to claim 1, wherein during the treatment ultrasound is applied to the solution at least periodwise or wherein the implant is irradiated with UV-light prior to and/or during and/or after the treatment in the solution.

15. The method according to claim 1, wherein prior to the treatment in the aqueous solution, a mechanically abrasive surface modification is carried out in the form of a blasting-treatment by sand blasting with use of particles with an average particle size of 0.05-0.25 mm or 0.25-0.5 mm, with a pressure between 1-10 bar.

16. The method according to claim 1, wherein prior to the treatment in the aqueous solution and possibly after a mechanically abrasive surface modification according to claim 15, a chemical surface modification is carried out, by treatment with concentrated sulphuric acid and/or hydrochloric acid and/or hydrofluoric acid and/or nitric acid or mixtures thereof, at a temperature above room temperature.

17. A method for the production of a metallic implant with a hydrophilic surface for at least partial insertion into hard tissue such as into a bone and/or into soft tissue, wherein the method comprises at least one step, in which at least one area, which is provided for partial insertion into hard tissue as into a bone and/or into soft tissue, is subjected, optionally after an antecedent mechanically and/or chemically abrasive surface modification, to a short-time treatment in an aqueous or organic solution of alkali- and/or alkaline-earth-hydroxides, or a mixture of these hydroxides, with a total concentration of alkali- and/or alkaline-earth-hydroxide in the range of 0.005M-0.5M, wherein the implant surface is stored and packaged in an alkaline solution after the treatment with the aqueous solution, wherein the alkaline solution is a solution of exclusively alkali- and/or alkaline-earth-hydroxides, or a mixture of these solutions.

18. The method according to claim 17, wherein the alkaline solution is a solution of sodium hydroxide, at a concentration of 0.0001-0.9 mole.

* * * * *